(12) United States Patent
Baril et al.

(10) Patent No.: US 11,304,714 B2
(45) Date of Patent: Apr. 19, 2022

(54) TISSUE SPECIMEN RETRIEVAL DEVICE WITH ASSISTED DEPLOYMENT

(71) Applicant: Covidien LP, Mansfield, MA (US)

(72) Inventors: Jacob C. Baril, Norwalk, CT (US); Saumya Banerjee, Hamden, CT (US); Justin J. Thomas, New Haven, CT (US); Roy J. Pilletere, North Haven, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 170 days.

(21) Appl. No.: 16/878,423

(22) Filed: May 19, 2020

(65) Prior Publication Data

US 2021/0361307 A1 Nov. 25, 2021

(51) Int. Cl.
*A61B 17/221* (2006.01)
*A61B 17/00* (2006.01)

(52) U.S. Cl.
CPC .. *A61B 17/221* (2013.01); *A61B 2017/00986* (2013.01); *A61B 2017/00991* (2013.01); *A61B 2017/2212* (2013.01)

(58) Field of Classification Search
CPC ........ A61B 2017/00287; A61B 17/221; A61B 2017/2212; A61B 2017/00986; A61B 2017/00991; A61B 17/32056; A61B 5/6858
USPC ................. 606/127, 110, 113, 114, 200, 151
See application file for complete search history.

(56) References Cited

U.S. PATENT DOCUMENTS

| | | | |
|---|---|---|---|
| 5,846,260 A | * | 12/1998 | Maahs .................... A61F 2/012 606/200 |
| 6,059,793 A | | 5/2000 | Pagedas |
| 6,156,055 A | | 12/2000 | Ravenscroft |
| 6,162,209 A | | 12/2000 | Gobron et al. |
| 6,171,317 B1 | | 1/2001 | Jackson et al. |
| 6,206,889 B1 | | 3/2001 | Bennardo |
| 6,224,612 B1 | | 5/2001 | Bates et al. |
| 6,228,095 B1 | | 5/2001 | Dennis |
| 6,248,113 B1 | | 6/2001 | Fina |
| 6,258,102 B1 | | 7/2001 | Pagedas |
| 6,264,663 B1 | | 7/2001 | Cano |
| 6,270,505 B1 | | 8/2001 | Yoshida et al. |
| 6,280,451 B1 | | 8/2001 | Bates et al. |

(Continued)

*Primary Examiner* — Wade Miles
*Assistant Examiner* — Kankindi Rwego
(74) *Attorney, Agent, or Firm* — Carter, DeLuca & Farrell LLP

(57) ABSTRACT

A tissue specimen retrieval device includes a first shaft having a pair of slots defined in a distal end thereof and a pair of windows defined proximally of the pair of respective slots. A second shaft is included having a bag brim attached thereto, the second shaft telescopically movable within the first shaft between a retracted position, wherein the bag brim is disposed within the first shaft and a partially deployed position wherein the bag brim partially deploys from the first shaft forming an enclosure for supporting the tissue bag thereon. A pair of hook members is included each having an arm, a first end engaged to the bag brim and a free end including a hook at a distal end thereof. Upon deployment, the hook of each hook member engages a respective window allowing each respective arm to pivot outwardly within respective slots to fully deploy the bag brim.

10 Claims, 3 Drawing Sheets

(56) References Cited

U.S. PATENT DOCUMENTS

| | | |
|---|---|---|
| 6,344,026 B1 | 2/2002 | Burbank et al. |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinsk et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2005/0267492 A1* | 12/2005 | Poncet ............... A61B 17/221 606/114 |

* cited by examiner

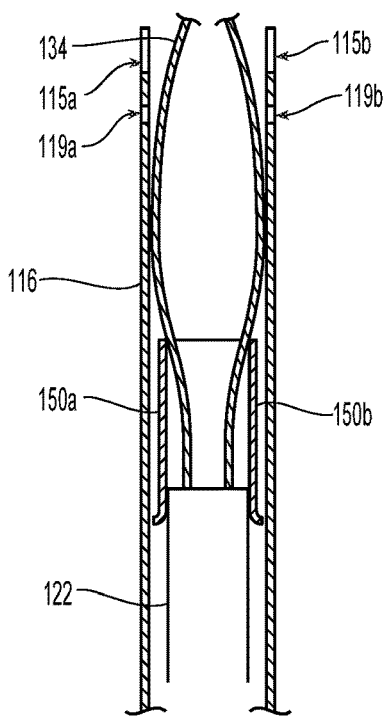
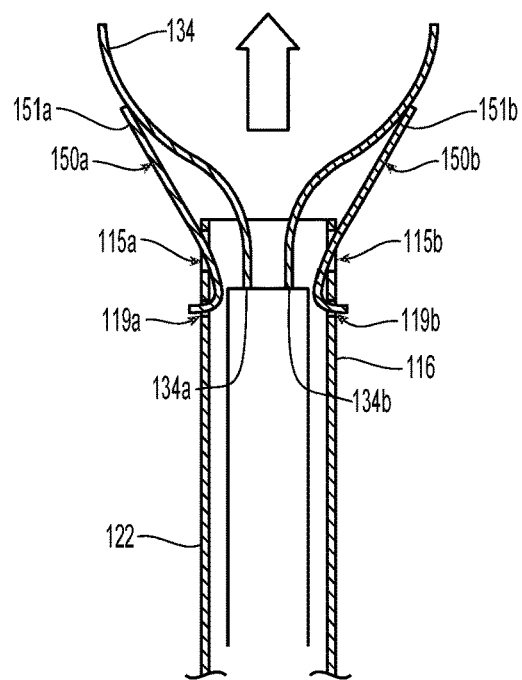
Fig. 3A    Fig. 3B
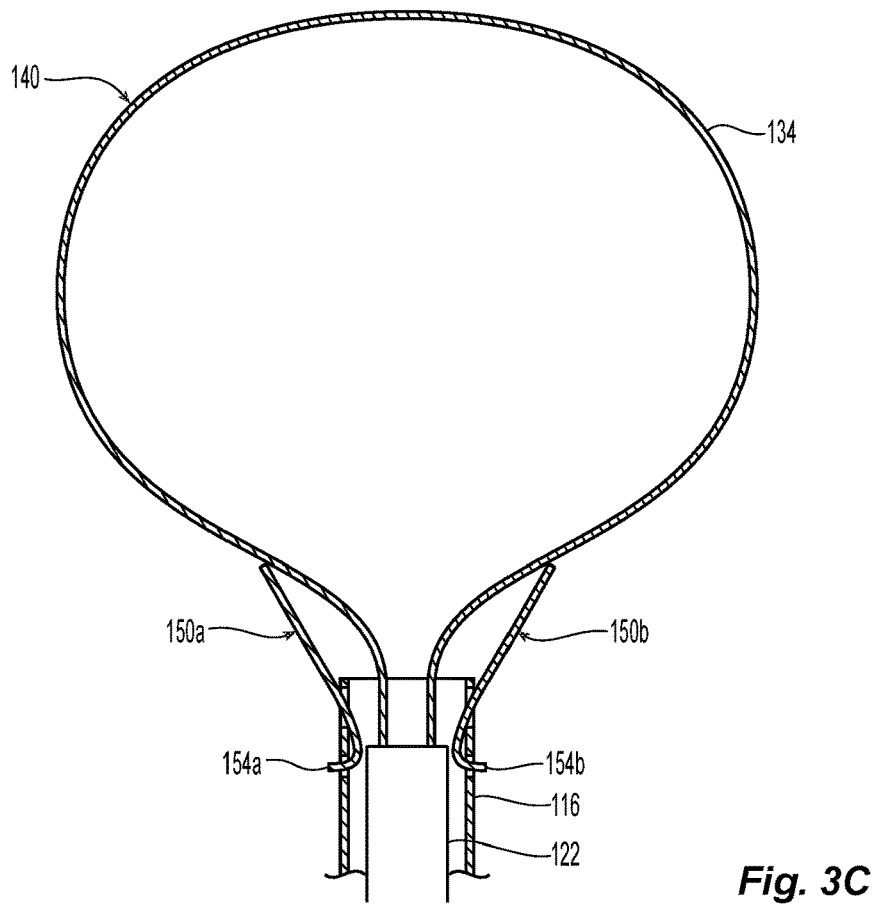
Fig. 3C

TISSUE SPECIMEN RETRIEVAL DEVICE WITH ASSISTED DEPLOYMENT

BACKGROUND

Technical Field

The present disclosure relates to tissue specimen retrieval from an internal body cavity and, more particularly, to tissue specimen retrieval devices and methods to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment. As a result, various specimen retrieval devices have been developed. These devices are typically made from shape memory alloys (e.g., Nitinol®) that are configured to facilitate deployment of the specimen bag and bag brim for specimen retrieval. However, these materials tend to be expensive compared to stainless steel and other materials.

Moreover, specimen retrieval devices often come from the manufacturer preloaded with a bag brim of a specific diameter which in most cases is over-sized for the tissue specimen.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is a tissue specimen retrieval device including a first shaft having a pair of elongated slots defined in a distal end thereof and a pair of corresponding windows defined proximally of the pair of respective slots. A second shaft is included having a bag brim attached thereto, the second shaft telescopically movable within the first shaft between a retracted position, wherein the bag brim is disposed within the first shaft and a partially deployed position wherein the bag brim at least partially deploys distally from the first shaft forming a substantially circular enclosure for supporting the tissue specimen bag thereon. A pair of hook members is included each having an arm, a first end operably engaged to the bag brim and a free end including a hook at a distal end thereof. Upon deployment, the hook of each hook member engages a respective window defined in the first shaft allowing each respective arm of each hook member to pivot outwardly within respective slots defined within the first shaft member to fully deploy the bag brim.

In aspects according to the present disclosure, the hook members are attached to opposing sides of the bag brim. In other aspects according to the present disclosure, the bag brim is made from a material selected from a group consisting of polymers, plastics, composite materials, surgical stainless steel, and aluminum.

In aspects according to the present disclosure, each hook member is attached to the bag brim by a rivet. In other aspects according to the present disclosure, the hook of each hook member includes geometry to facilitate removal from each window upon retraction of the bag brim within the first shaft.

Provided in accordance with aspects of the present disclosure is a tissue specimen retrieval device including a first shaft having a pair of elongated slots defined in a distal end thereof and a pair of corresponding windows defined proximally of the pair of respective slots. A second shaft is included having a bag brim attached thereto, the second shaft telescopically movable within the first shaft between a retracted position, wherein the bag brim is disposed within the first shaft and a first deployed position wherein the bag brim at least partially deploys distally from the first shaft forming a substantially circular enclosure for supporting an open end of the tissue specimen bag thereon. A pair of hook members is included each having an arm, a first end operably engaged to the bag brim and a free end including a hook at a distal end thereof. Upon deployment from the first deployed position to a second deployed position, the hook of each hook member engages a respective window defined in the first shaft allowing each respective arm of each hook member to pivot outwardly within respective slots defined within the first shaft member to more fully deploy the bag brim and maximize the open end of the tissue specimen bag.

In aspects according to the present disclosure, the hook members are attached to opposing sides of the bag brim. In other aspects according to the present disclosure, the bag brim is made from a material selected from a group consisting of polymers, plastics, composite materials, surgical stainless steel, and aluminum.

In aspects according to the present disclosure, each hook member is attached to the bag brim by a rivet. In other aspects according to the present disclosure, the hook of each hook member includes geometry to facilitate removal from each window upon retraction of the bag brim within the first shaft.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIG. 3A is a top, internal view of the tissue specimen retrieval device of FIG. 1 shown prior to deployment;

FIG. 3B is a top, internal view of the tissue specimen retrieval device of FIG. 1 shown during deployment;

FIG. 3C is a top, internal view of the tissue specimen retrieval device of FIG. 1 shown fully deployed;

DETAILED DESCRIPTION

Figure 1:
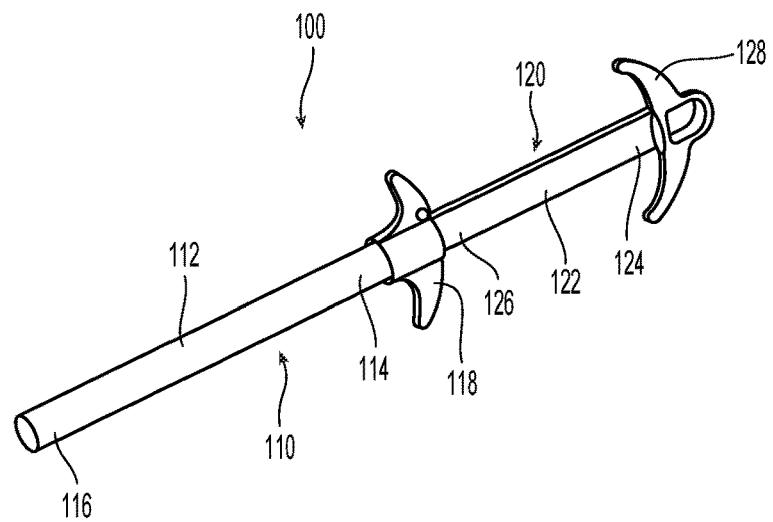
FIG. 1 is a perspective view of a tissue specimen retrieval device provided in accordance with aspects of the present disclosure, showing a bag brim disposed in a retracted position within the tissue specimen outer shaft.
Figure 2:
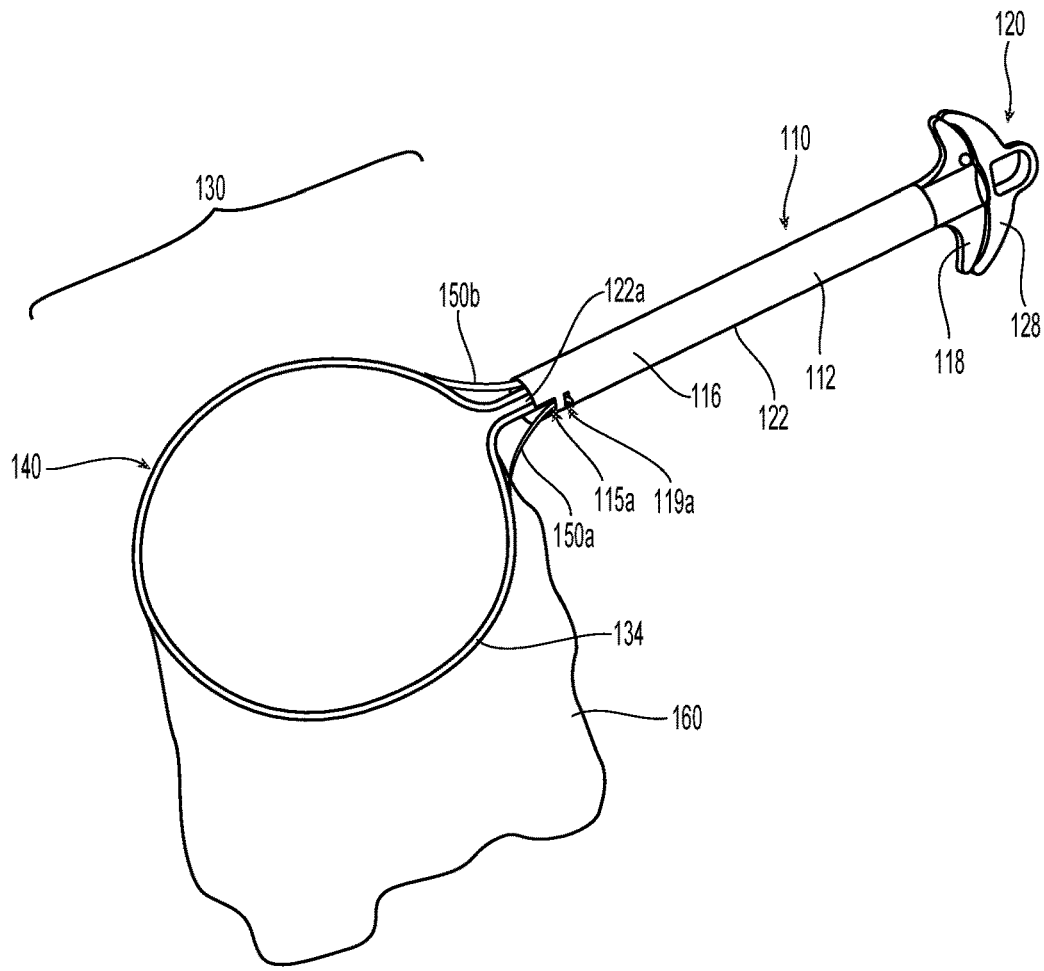
FIG. 2 is a perspective view of the tissue specimen retrieval device of FIG. 1, disposed in a deployed position showing a bag brim supporting a specimen bag.
Figure 4:
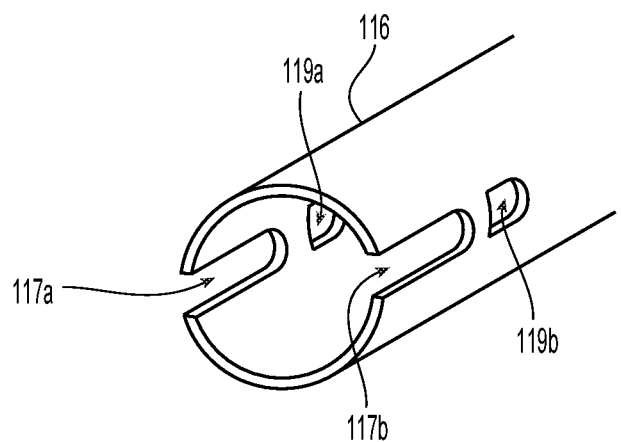
FIG. 4 is an enlarged, perspective view of a distal end of the outer shaft of the tissue specimen retrieval device.

Turning to FIGS. 1-2, a tissue specimen retrieval device provided in accordance with the present disclosure is shown generally identified by reference numeral 100. Tissue specimen retrieval device 100 includes a first body 110, a second body 120, and an end effector assembly 130 including a bag brim 140 and a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2), wherein end effector assembly 130 extends distally from first shaft 112 to deploy the bag brim 140 and specimen bag 160. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2) to move tissue specimen retrieval device 100 from the retracted position (FIG. 1), wherein end effector assembly 130 is disposed within first shaft 112, to the deployed position (FIG. 2), wherein end effector assembly 130 extends distally from first shaft 112.

Referring to FIGS. 3A-3C, end effector assembly 130, as noted above, is supported at distal end portion 126 of second shaft 122. End effector assembly 130, more specifically, includes bag brim 140 extending distally from distal end portion 126 of second shaft 122 and a specimen bag 160 (FIG. 2) supported on the bag brim 140. Bag brim 140 includes a substantially circular arm 134 that extends from a distal face of shaft 122. Typically, bag brim 140 is made from a shape memory alloy (e.g., Nitinol®) that is configured to facilitate deployment of the bag brim 140 for specimen retrieval. Other types of materials may be cheaper to utilize for the bag brim 140, e.g., polymers, plastics, composite materials, surgical stainless steel, aluminum, etc., but need to be reinforced to insure reliable deployment. Moreover, the bag brim 140 may be designed to be substantially flat (e.g., thin, band-like material) to provide strength for supporting the specimen bag 160 while still being flexible to facilitate expansion and retraction thereof.

The presently disclosed end effector assembly 130 and bag brim 140 may be made from materials other than shape memory alloys (e.g., Nitinol®) while still promoting reliable and consistent deployment. For the purposes herein, the bag brim 140 is made from surgical stainless steel although other similar type materials are also envisioned.

Bag brim 140 is made from high yield stainless steel that may be heat treated after initial shaping. More specifically, arm 134 includes free ends 134a and 134b that operably engage distal end 126 of shaft 122 to form a band-like support for supporting the specimen bag 160. The bag brim 140, upon deployment from end 116 of shaft 112, is configured to open to a generally circular configuration. Generally, since stainless steel is not as reliable as Nitinol®, the specimen bag 160 may not consistently deploy to a desired and/or useful configuration.

Figure 5:
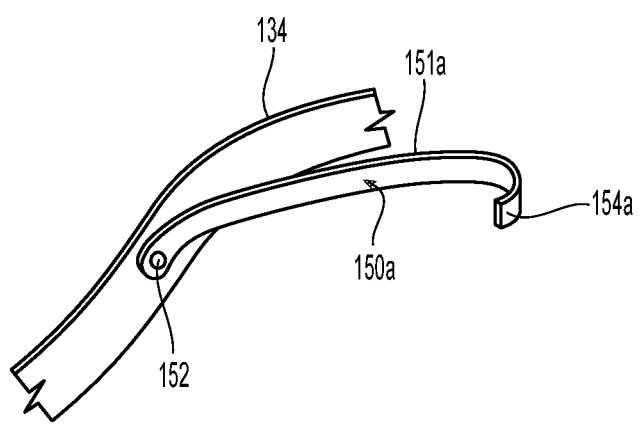
FIG. 5 is an enlarged, perspective view showing a deployment hook for use with an arm of the bag brim to facilitate deployment of the tissue specimen device.

A pair of hook members 150a, 150b is included with the end effector assembly 130 to facilitate reliable and consistent deployment of the specimen bag 160 to a desired configuration. More particularly, in a retracted configuration (FIG. 3A), a distal end 154a, 154b of each respective hook member 150a, 150b is configured to rest against an inner peripheral surface of shaft 116. The opposite end of each hook member 150a, 150b is riveted or otherwise secured to the bag arm 134, e.g., by a rivet 152 (FIG. 5).

The distal end 116 of shaft 112 includes a pair of opposing slots 117a, 117b defined therealong extending proximally therefrom along with a corresponding pair of hook windows 119a, 119b defined proximally relative thereto. As explained in more detail below, slots 117a, 117b are configured to allow the respective arms 151a, 151b of each hook member 150a, 150b to pivot outwardly to facilitate deployment of the bag brim 140 when the distal end 154a, 154b of each hook member 150a, 150b is engaged within hook windows 119a, 199b.

In use, the bag brim 140 is initially disposed in a collapsed, retracted configuration within a distal end 116 of shaft 112 (FIG. 3A). In the retracted configuration, the bag brim 140 is collapsed to fit within the inner peripheral surface of shaft 112 and the distal ends 154a, 154b of hook members 150a, 150b are sandwiched between the distal end of shaft 122 and the inner peripheral surface of the distal end 116 of shaft 112.

Upon initial deployment, the shaft 122 is pushed relative to shaft 112 to expose the bag brim 140 from the distal end 116 of shaft 112. As mentioned above, the spring-like properties of the surgical steel of the bag brim 140 cause the bag brim 140 and specimen bag 160 to at least partially open upon deployment. As shaft 122 is continually pushed distally within shaft 112, the distal ends 154a, 154b of the hook members 150a, 150b are configured to engage respective hook windows 119a, 119b preventing further distal advancement of shaft 122 relative to shaft 112 (FIG. 3B).

Once the distal ends 154a, 154b of the hook members 150a, 150b are engaged, the arms 151a, 151b of the hook members 150a, 150b are free to rotate outwardly within respective slots 117a, 117b to force the bag brim 140 to deploy further and open the mouth of the specimen bag fully and to a more desirable configuration (FIG. 3C). The specimen bag is now fully deployed and ready for specimen containment.

Once a tissue specimen is captured within the specimen bag 160, handle 128 may be retracted or pulled proximally relative to handle 118 to pull arm 134 back within shaft 112 and reduce the diameter of the bag brim 140. The geometry of the distal ends 154a, 154b of the hook members 150a, 150b may be configured to cam out of the respective hook windows 119a, 119b during retraction of shaft 122 within the distal end 116 of shaft 112. Bag brim 140 may include features that close off the opening of the bag brim 140 when fully retracted. Other features may be included that sever the bag brim 140 from the bag 160 when fully retracted.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
    a first shaft including a pair of elongated slots defined in a distal end thereof and a pair of corresponding windows defined proximally of the pair of respective slots;
    a second shaft including a bag brim attached thereto, the second shaft telescopically movable within the first shaft between a retracted position, wherein the bag brim is disposed within the first shaft and a partially deployed position wherein the bag brim at least partially deploys distally from the first shaft forming a substantially circular enclosure for supporting a tissue specimen bag thereon; and
    a pair of hook members each having an arm, a first end operably engaged to the bag brim and a free end including a hook at a distal end thereof, wherein, upon deployment, the hook of each hook member engages a respective window defined in the first shaft allowing each respective arm of each hook member to pivot outwardly within respective slots defined within the first shaft member to fully deploy the bag brim.

2. The tissue specimen retrieval device according to claim 1, wherein the hook members are attached to opposing sides of the bag brim.

3. The tissue specimen retrieval device according to claim 1, wherein the bag brim is made from a material selected from a group consisting of polymers, plastics, composite materials, surgical stainless steel, and aluminum.

4. The tissue specimen retrieval device according to claim 1, wherein each hook member is attached to the bag brim by a rivet.

5. The tissue specimen retrieval device according to claim 1, wherein the hook of each hook member includes geometry to facilitate removal from each window upon retraction of the bag brim within the first shaft.

6. A tissue specimen retrieval device, comprising:
    a first shaft including a pair of elongated slots defined in a distal end thereof and a pair of corresponding windows defined proximally of the pair of respective slots;
    a second shaft including a bag brim attached thereto, the second shaft telescopically movable within the first shaft between a retracted position, wherein the bag brim is disposed within the first shaft and a first deployed position wherein the bag brim at least partially deploys distally from the first shaft forming a substantially circular enclosure for supporting an open end of a tissue specimen bag thereon; and
    a pair of hook members each having an arm, a first end operably engaged to the bag brim and a free end including a hook at a distal end thereof, wherein, upon deployment from the first deployed position to a second deployed position, the hook of each hook member engages a respective window defined in the first shaft allowing each respective arm of each hook member to pivot outwardly within respective slots defined within the first shaft member to more fully deploy the bag brim and maximize the open end of the tissue specimen bag.

7. The tissue specimen retrieval device according to claim 6, wherein the hook members are attached to opposing sides of the bag brim.

8. The tissue specimen retrieval device according to claim 6, wherein the bag brim is made from a material selected from a group consisting of polymers, plastics, composite materials, surgical stainless steel, and aluminum.

9. The tissue specimen retrieval device according to claim 6, wherein each hook member is attached to the bag brim by a rivet.

10. The tissue specimen retrieval device according to claim 6, wherein the hook of each hook member includes geometry to facilitate removal from each window upon retraction of the bag brim within the first shaft.

* * * * *